United States Patent [19]

Herman

[11] Patent Number: 5,718,897
[45] Date of Patent: Feb. 17, 1998

[54] ENHANCING KERATINOCYTE MIGRATION AND PROLIFERATION

[75] Inventor: Ira M. Herman, Newton, Mass.

[73] Assignee: Trustees of Tufts College, Medford, Mass.

[21] Appl. No.: 777,267

[22] Filed: Dec. 31, 1996

Related U.S. Application Data

[63] Continuation-in-part of Ser. No. 484,382, Jun. 7, 1995.
[51] Int. Cl.⁶ .......................... A61K 38/46; A61K 38/00
[52] U.S. Cl. ................................. 424/94.67; 514/2
[58] Field of Search ........................... 424/94.67; 514/2

[56] References Cited

U.S. PATENT DOCUMENTS

| 5,393,792 | 2/1995 | Stern et al. | 514/777 |
| 5,514,370 | 5/1996 | Stern et al. | 424/78.06 |

OTHER PUBLICATIONS

—, "Exp. Cell. Res." 196:114–120 (1991).

*Primary Examiner*—John W. Rollins
*Attorney, Agent, or Firm*—Roland Plottel; John D. Uphan

[57] ABSTRACT

A method of enhancing the migration and proliferation of keratinocytes in wound healing or in the growth of artificial skin grown in vitro. The wound is contacted with (a) an effective amount of purified Clostridiopeptidase A collagenase that is substantially free from other proteinases and (b) an amount of a growth factor that increases the effects of said collagenase. The artificial skin is grown upon biomatrices previously synthesized by living cells and digested with Clostridiopeptidase A collagenase while in the presence of (a) an effective concentration of purified Clostridiopeptidase A collagenase substantially free from other proteinases and (b) a growth factor in a concentration effective to increase the effectiveness of said collagenase.

16 Claims, 10 Drawing Sheets

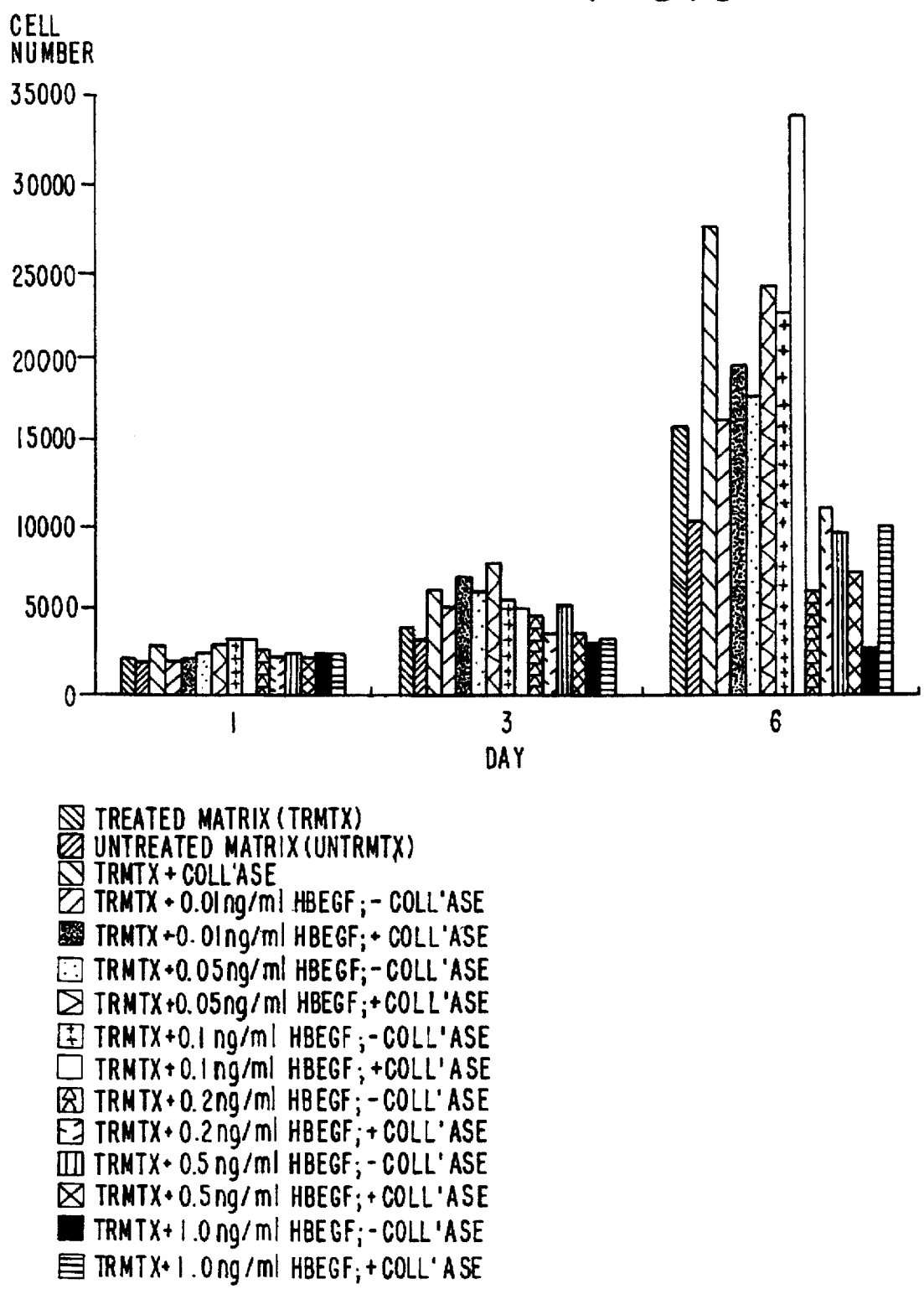

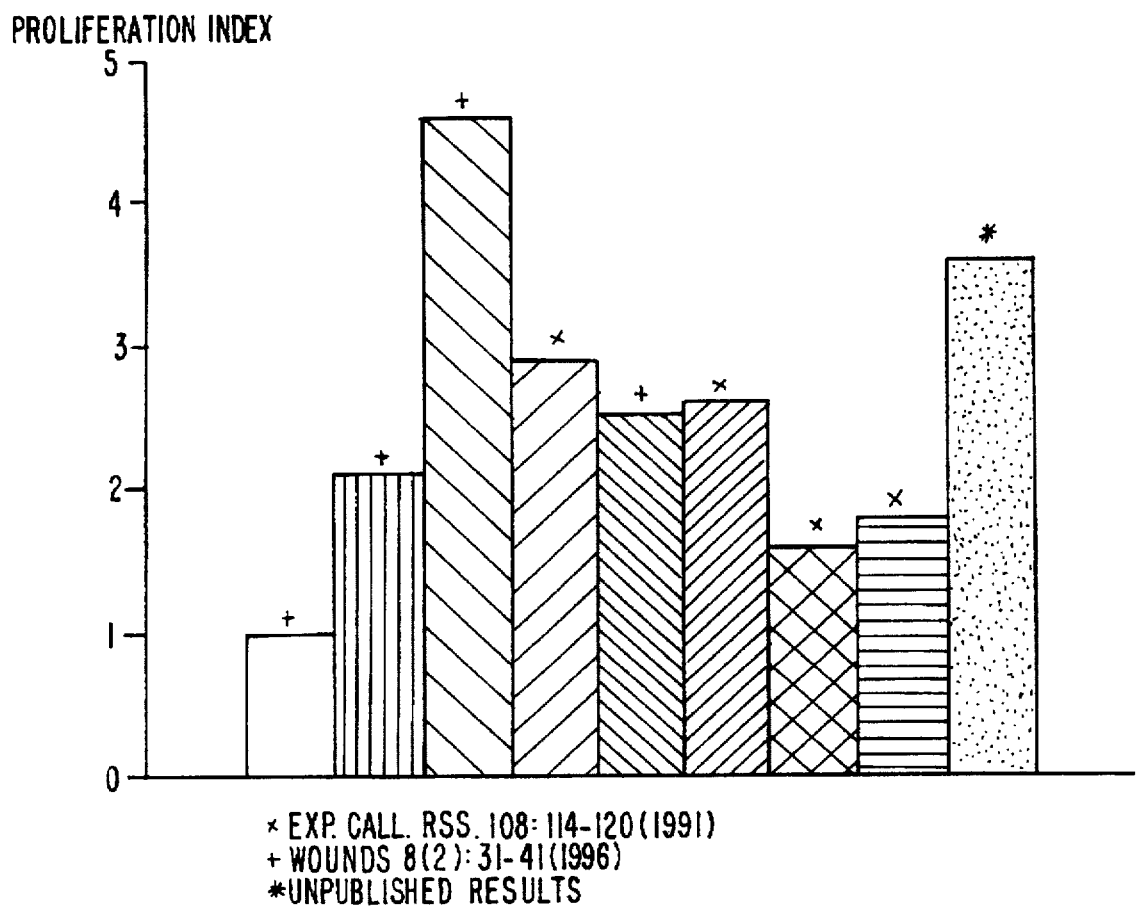

5,718,897

ENHANCING KERATINOCYTE MIGRATION AND PROLIFERATION

CROSS-REFERENCE TO RELATED APPLICATION

This application is a continuation-in-part of my copending application Ser. No. 08/484,382, filed Jun. 7, 1995, the contents of which are hereby incorporated by reference.

FIELD OF THE INVENTION

The present invention generally relates to the use of growth factors in conjunction with a particular form of collagenase to increase the motility and growth of keratinocytes.

BACKGROUND OF THE INVENTION

Keratinocytes are the predominate cell type of the epidermis. They arise by mitotic division from the stem cells constituting the deepest layer of the epidermis. The keratinocytes migrate upwardly, changing in structure and function until they become mature keratinized cells at the surface of the skin and are eventually sloughed off.

The rate of healing of wounds is affected, inter alia, by the rate of keratinocyte migration and proliferation.

Collagenase has been used to ameliorate various pathologic conditions of the body, and the effect of endogenesis collagenase on certain body functions has been studied.

Chiulli and Wegman, U.S. Pat. No. 3,705,083 (1972), produced from Clostridium histolyticum a combination of collagenase and another protease, and used it in ointment to debride necrotic tissue from dermal lesions such as burns, infected wounds and ulcers. This ointment has been on the market for the past 25 years. They also proposed using the combination as an injectable solution to facilitate internal sloughing and reabsorption of physiologically antagonistic tissue.

Sussman, U.S. Pat. No. 3,678,158 (1972), injected purified collagenase into herniated intravertebral discs.

Cope, U.S. Pat. No. 4,174,389 (1979), used Clostridiopeptidase A collagenase for the selective lysis of collagen fibrils in the vitreous of the eye.

Pinnell, U.S. Pat. No. 4,524,065 (1985), treated mammalian cicatrices such as acne scars, keloids and other hypertrophic scars by intralesional injection of purified collagenase.

Wehling, U.S. Pat. No. 5,173,295 (1992) used purified collagenase to enhance regeneration of injured nerves.

Gelbard, U.S. Pat. No. 4,338,300 (1982), injected collagenase into the plaques of Peyronie's Disease.

W. E. Zimmerman, Collagenase, Innie Mandel, ed., London, 1972, Gordon & Breach, (pp. 131–141) "The Importance of Collagenase for the Local Treatment of Major Burns," states that collagenase used on burns exerts a concomitant beneficial effect on the formation of tissue proliferations and may thus be used to advantage in the treatment of varying types of wounds.

Herman, Journal of Cardiovascular Pharmacology 22 (Suppl. 4): S25–S36 (1993), "Molecular Mechanisms Regulating the Vascular Endothelial Cell Motile Response to Injury," reported that a commercial non-homogeneous preparation of bacterial collagenase routinely used for the isolation of vascular cells from blood vessel segments increased the rate of migration of vascular endothelial cells injured on an epithelial cell-synthesized matrix in vitro from two to five times the rate compared to identical populations of vascular endothelial cells recovering from injury on intact matrix.

Herman, Wounds 8(2): 33–41 (1996), "Stimulation of Human Keratinocyte Migration and Proliferation In Vitro: Insight into the Cellular Responses to Injury and Wound Healing," reports the work described in U.S. Ser. No. 08/484,382, the parent of this continuation-in-part application.

The parent application, Ser. No. 08/484,382, teaches the enhancement of the migration and proliferation of keratinocytes in wound healing by contacting same with Clostridiopeptidase A collagenase (EC 3.4.24.3), obtained by fermentation of Clostridium histolyticum, that has been purified to be substantially free from other proteinases. Preferably, an open wound in the skin is treated by contacting exposed sub-cellular matrix with the said purified collagenase in an amount effective to enhance the rate of migration of keratinocytes bordering the wound edges. Contacting keratinocytes means contacting them directly, and/or indirectly by contacting their growth substrate upon which they grow and divide, the sub-cellular matrix.

THE INVENTION

The invention taught in the present application is an improvement wherein the action of the purified collagenase is enhanced by growth factors.

By growth factor I include all mammalian growth factors both naturally occurring and formed by recombinant DNA technology. Preferred are those, which bind with high affinity and specificity to keratinocytes; and those which so bind and bind at low affinity to the sub-cellular matrix of skin. During the practice of the invention it is believed that the growth factor binds preferentially to high-affinity receptors of the keratinocytes exchanging from the low-affinity matrix binding sites. A particularly preferred group is the heparin-binding growth factor family. Heparin-binding epidermal-like growth factor (hb-EGF) is especially preferred. Other such growth factors of the family include FGF-1 (acidic fibroblast growth factor), FGF-2 (basic fibroblast growth factor), and FGF-4 (KGFG, Kaposis fibroblast growth factor). Other growth factor families of choice include keratinocyte growth factors and epidermal growth factors.

The wound is treated by contacting Clostridiopeptidase A collagenase substantially free from other proteinases with the sub-cellular matrix, or with portions of the wound nearer the surface of the skin (which latter contacting is termed herein "exogenous"), or both. The growth factor is also so contacted. Superior results are obtained when the collagenase is both in sub-cellular contact and exogenous. A useful procedure is first to treat the sub-cellular matrix underlying the wound, some of which may or may not be exposed, by injecting a solution of the purified Clostridiopeptidase A collagenase, allowing some time to pass, e.g. a few minutes up to an hour or more, and then treat the wound with an exogenous solution of the purified collagenase and the growth factor. One growth factor, or two or more, may be used.

The purified collagenase, and one or more growth factors, are preferably applied, separately or together, in an aqueous solution, e.g. dissolved in phosphate-buffered saline. They may also be used in admixture with other pharmaceutically acceptable liquid or solid carriers, including slow release carriers. The nature and use of such carriers is within the skill of the art.

Suitable concentrations of the purified Clostridiopeptidase A may range from about 0.5 ABC units collagenase/ml or less up to about 150 ABC units/ml or more, i.e. about 5 µg/ml or less up to about 1,500 µg/ml or more. Concentrations often will be in the range of about 2 to about 50 ABC units/ml. The amount of the purified collagenase applied will be sufficient to increase substantially the migration rate of the keratinocytes towards and at the wound edges, preferably at least three-fold over the rate that would prevail without the treatment. Of course, the larger the wound the greater the amount of the purified collagenase to be used. A preferred effective amount is usually about 4 ABC units per square centimeter of matrix and 4 ABC units per cubic centimeter of tissue volume. Also, the more body fluid present or expected to be present in the wound, the higher the concentration of collagenase solution that will be used. The physician will use his/her professional judgment in these matters.

Suitable concentrations of growth factor may range from about 0.01 ng/ml or less up to about 10 ng/ml or more, preferably about 0.1 ng/ml or less up to about 0.5 ng/ml (eg. for hb-EGF) or more. The amount of the growth factor applied will be sufficient to increase the effectiveness of the collagenase. As the concentration of growth factor is increased from a small amount, relative to a given concentration of collagenase, the favorable effect on keratinocytes increases to a maximum then decreases; thus in a given situation it would be counter-productive to exceed the maximum. In the same manner as stated above with respect to collagenase, the amount and concentration of growth factor used will be a function of wound size and body fluid in the wound, and physician judgment will be used.

The potency assay of collagenase is based on the digestion of undenatured collagen (from bovine tendon) at pH 7.2 and 37° C. for 20–24 hours. The number of peptide bonds cleaved are measured by reaction with ninhydrin. Amino groups released by a trypsin digestion control are subtracted. One net ABC unit of collagenase will solubilize ninhydrin reactive material equivalent to 1.09 nanomoles of leucine per minute.

The assay of collagenases for other proteinases is based on ability to digest casein. This caseinase assay procedure combines (1) the idea of Reimerdes and Klostermeyer [Methods Enzymol 45: 26–28 (1976)] to determine the amount of primary amino groups present in the trichloroacetic acid-soluble digestion products with (2) the method of Udenfriend et al. [Science 178: 871–2 (1972)] to detect the primary amino groups fluorometrically. The sample is incubated with added casein, which is not soluble, at 37° C. for 20–22 hours. The sample is quenched with trichloroacetic acid and the undigested casein is then centrifuged out. Solubilized peptides result from the action of caseinase in the sample on the added casein. Each peptide molecule has a terminal primary amine group. Fluorescamine™ is added to the supernatant and reacts with primary amine groups producing fluorescent molecules. The fluorescence is measured and a calculation gives a caseinase activity as FFC units.

This invention has particular value applied to human wounds. It is useful in treating wounds of all mammals, especially those of economic value, e.g. horses, mules, cattle, sheep, goats, swine, dogs, cats, and other agricultural and domesticated animals fur-bearing animals, zoo animals including aquatic species.

The present invention in another aspect provides a method of enhancing the migration and proliferation of keratinocytes in the growth of mammalian, e.g. human, artificial skin in vitro by growing the artificial skin upon bio-matrices previously digested with purified Clostridiopeptidase A collagenase as described in Herman and in the presence of added Clostridiopeptidase A collagenase that has been purified to be substantially free from other proteinases. Artificial skins are useful as temporary skin grafts for burns and ulcers, and are used for testing of cosmetics and household cleansers in vitro.

In applying the present invention, the artificial skin is grown upon living biomatrices previously digested with the purified Clostridiopeptidase A collagenase described herein (to optimize attachment, migration and proliferation), as described in Herman; growth factor(s) may also be included. The purified Clostridiopeptidase A collagenase described herein, and one or more growth factors as described herein, are added to the growth medium, thereby enhancing the migration and proliferation of keratinocytes. Concentrations in the growth medium may range from about 0.5 ABC units collagenase/ml or less to about 150 ABC units/ml or more, and from about 0.01 ng/ml or less to about 10 ng/ml or more of growth factor.

Some examples of artificial skins whose growths can be favorably affected by this invention follow.

Advanced Tissue Sciences of La Jolla, Calif. has marketed Dermagraft™ as a skin substitute. A mesh scaffold made from lactic acid-glycolic acid copolymer, about 90 µ thick with openings of about 200–220 µm was seeded with skin fibroblasts from neonatal foreskins. The cells bridge sufficiently to secrete skin proteins and proteoglycans. See Hubbell, JA et al. Chemical and Engineering News pp. 42–53 (Mar. 13, 1995).

Graftskin™ has been introduced by Organogenesis of Canton, Mass. See Nolte CJ et al. Journal of Anatomy 185 (Pt. 2): 325-33 (1944 October)

Advanced Tissue Sciences has also marketed Skin²™ as a skin substitute for in vitro testing of cosmetics, household chemicals and other products. See Stoppie P et al. European Journal of Morphology 31 (1–2): 26–9 (1993).

See also Hansbrough JF et al., Journal of Burn Care & Rehabilitation 14(5): 485–94 (1993).

EXPERIMENTAL

In the following descriptions: SECTION A, taken verbatim from the parent application, illustrates the effects of collagenase of various purities. SECTION B illustrates the present invention utilizing growth factors.

SECTION A

The effect of collagenases of varying purities on the motility and proliferation of keratinocytes was determined in vitro, employing sub-cellular matrices synthesized from vascular endothelial cells.

Vascular endothelial cell culture

Endothelial cells are isolated from living bovine vessel segments. Rings of aortae are obtained on ice from an abattoir sutured at the ends and filled with balanced salts (BSS). Endothelial cells are released from the intima using 0.1% collagenase dissolved in BSS by incubation at 37° C. for 30 minutes-one hour. Cells are pelleted at 200 g for 5 minutes at room temperature and the resultant pellet resuspended in growth media containing 5% calf serum. Cells are plated into tissue culture at 50K cells/25 cm². Following growth to confluence, cells are typsinized and passaged at 1:5 split. Cells are used between passages 5–15.

Endothelial-derived matrix

One week post-confluent endothelial cells are washed with BSS prior to lysis in sterile solution containing 0.5% sodium deoxycholate in 0.015M NaCl, 0.001M EGTA buffered with 0.02M Tris-Cl, pH 7.8 with 0.001M phenyl methyl sulfonyl fluoride (PMSF) as a protease inhibitor. Two room temperature detergent treatments, each lasting 15 minutes, are followed by five washes with BSS, each wash lasting 5 minutes. Keratinocytes are then plated directly and sterilely onto washed matrices or matrices digested with collagenase solutions.

Treating matrices with collagenases

Endothelial matrices, prepared as described above are treated for 60 minutes at 37° C. with various preparations of collagenases dissolved in BSS (0.9% sodium chloride) containing 2 mM $CaCl_2$. Collagenase dose ranges from 0–128 U/ml; 1 U/ml=10 µg/ml collagenase. (U means ABC units). Matrices treated with the enzyme are then washed with BSS without calcium and keratinocytes and then plated.

Human keratinocytes

At circumcision, foreskins are placed into GIBCO Keratinocyte-SFM containing Gentamycin (Cat.nos. 17005–018 and 157–015) at 5 µg/ml. Tissue is then rinsed in BSS with gentamycin prior to cutting into pieces of 3–4 $mm^2$. Tissue pieces are then incubated for 18 hrs at 4° C. in 25 U/ml dispase (Collaborative Research cat.no. 40235). After dispase incubation, the epidermal layer of human keratinocytes is lifted from the dermis and placed into 15 ml centrifuge tubes containing trypsin-EDTA (2 ml). Following a 15 minute incubation at 37° C., cells are sedimented and plated in Keratinocyte-SFM at an initial seeding density of $3\times10^6$ cells/T/75 $cm^2$ /flask. cells are incubated and passaged using trypsin-EDTA when the flask is 60–70% confluent.

Motility and growth studies

For cell motility (wound healing) studies, keratinocytes are plated at near-confluent densities on intact or collagenase-treated matrices (100K cells/$cm^2$). Cells plated on glass microscope cover slides with matrices attached are then placed into a specially-designed culture chamber that mounts on the stage of an inverted, interference or phase contrast light microscope. Cells are warmed to 37° C. while viewed using video-enhanced optics coupled with computer-assisted imaging work station and software developed in the lab to automatically track living cell migration (Cell Tracker, Askey and Herman, 1988; Computers and Biomedical Res. 21:551–61). Keratinocytes bordering artificially created wounds made with fire-polished pasteur pipets, or keratinocytes at the edge of intact sheets, are then recorded for motility as a function of matrix condition.

For cell proliferation studies, keratinocytes are plated in triplicate onto plastic or matrix (intact or collagenase treated; doses from 0–64 U/ml, with 4 U/ml sufficient to deliver maximal proliferative responses seen within 7 days post-plating) at 2–5K cells/$cm^2$. Cells are fed on alternate days with Keratinocyte-SFM and triplicate wells of cells counted directly using a Coulter Counter, ZF. Cell counts, together with errors of the mean are plotted as a function of time and condition using Kaleidograph, a software support compatible with a PC Macintosh computer workstation in the lab.

Crude Collagenase

This was obtained substantially as described by Chiulli and Wegman in U.S. Pat. No. 3,705,083 (see page 1 above), with minor modifications. It is the powder used as the active ingredient in Santyl$^R$ Ointment. The collagenase content ranges from 100–300 ABC units per mg, and the proteinase content ranges from 30 to 240 FFC units/mg.

Cleaned-Up Collagenase

Crude Collagenase was suspended in distilled water and after thorough stirring was centrifuged. The centrifuge tubing were decanted and the supernatant was again centrifuged. The resultant clarified solution was "cleaned up" product.

ABC Purified Collagenase

This was prepared from crude collagenase by chromatography substantially eliminating other proteinases. The purified collagenase used contained only about 0.1 FFC units proteinases per mg.

Pool 3A

This was a combination of fractions discarded in the chromatography yielding Purified Collagenase.

Clostripain

A proteinase present in crude. This sample was a commercially available clostripain.

The collagenases were provided by Advance Biofactures Corporation of Lynbrook, N.Y. 11563.

In the following tests, the concentration of collagenase used in all of the samples of varying purities was 4 ABC units per ml.

BRIEF DESCRIPTION OF THE DRAWINGS

FIGS. 3–10 are graphs illustrating aspects of the invention.

DESCRIPTION OF THE PREFERRED EMBODIMENTS

Figure 1:
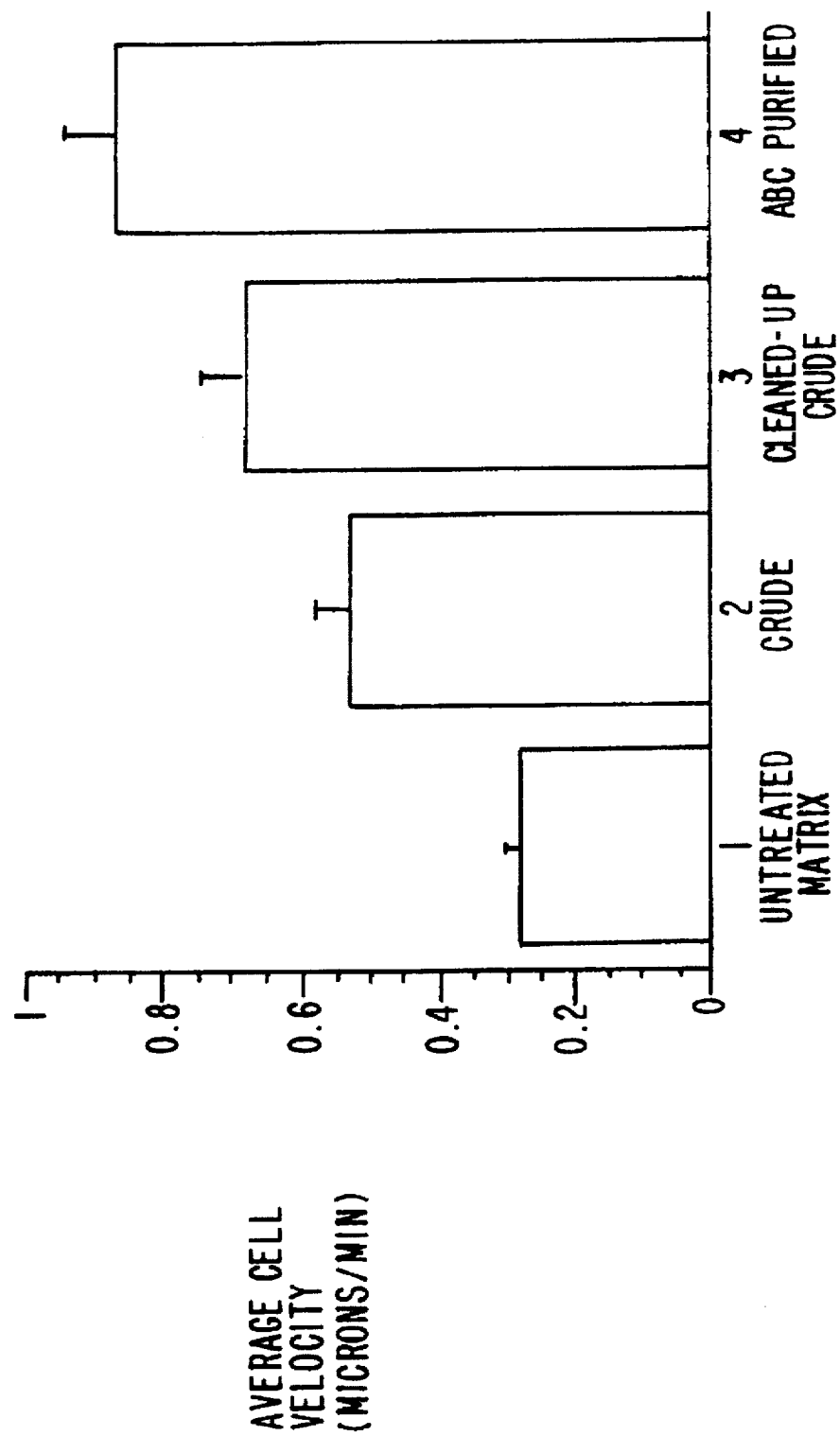
FIG. 1 presents graphically the motility (migration) data.
Figure 2:
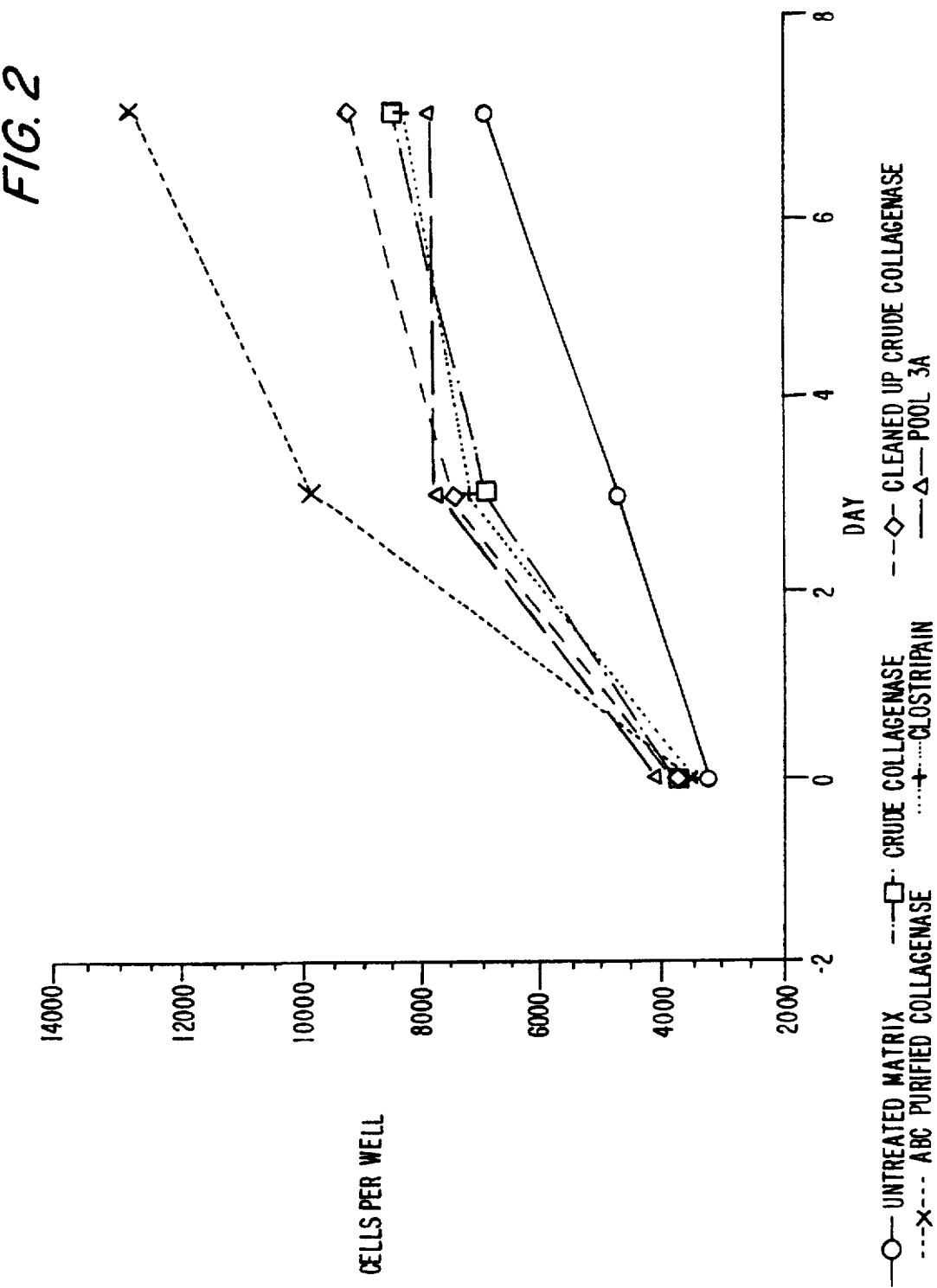
FIG. 2 presents graphically the proliferation data.
Figure 3:
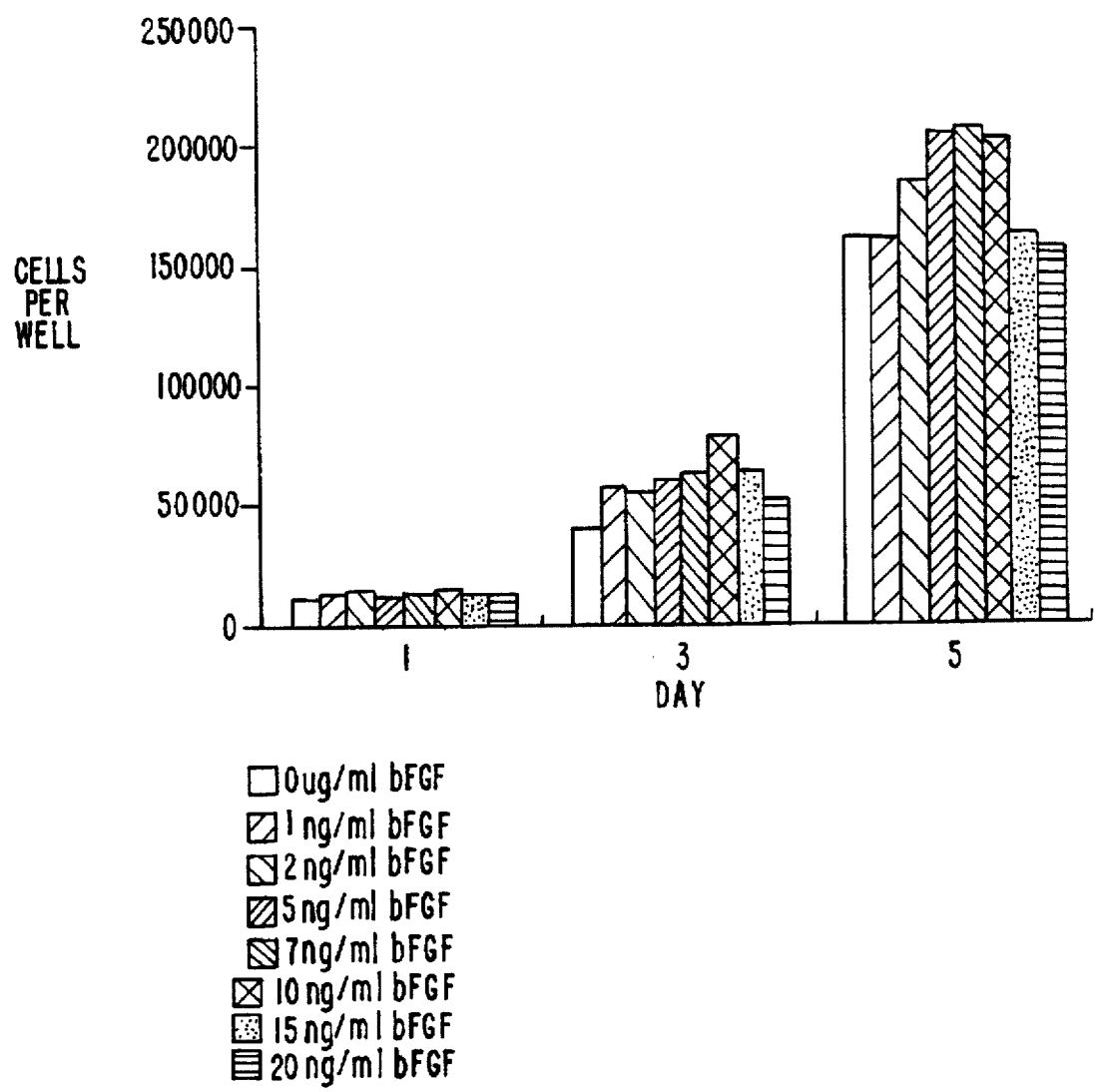
Figure 4:
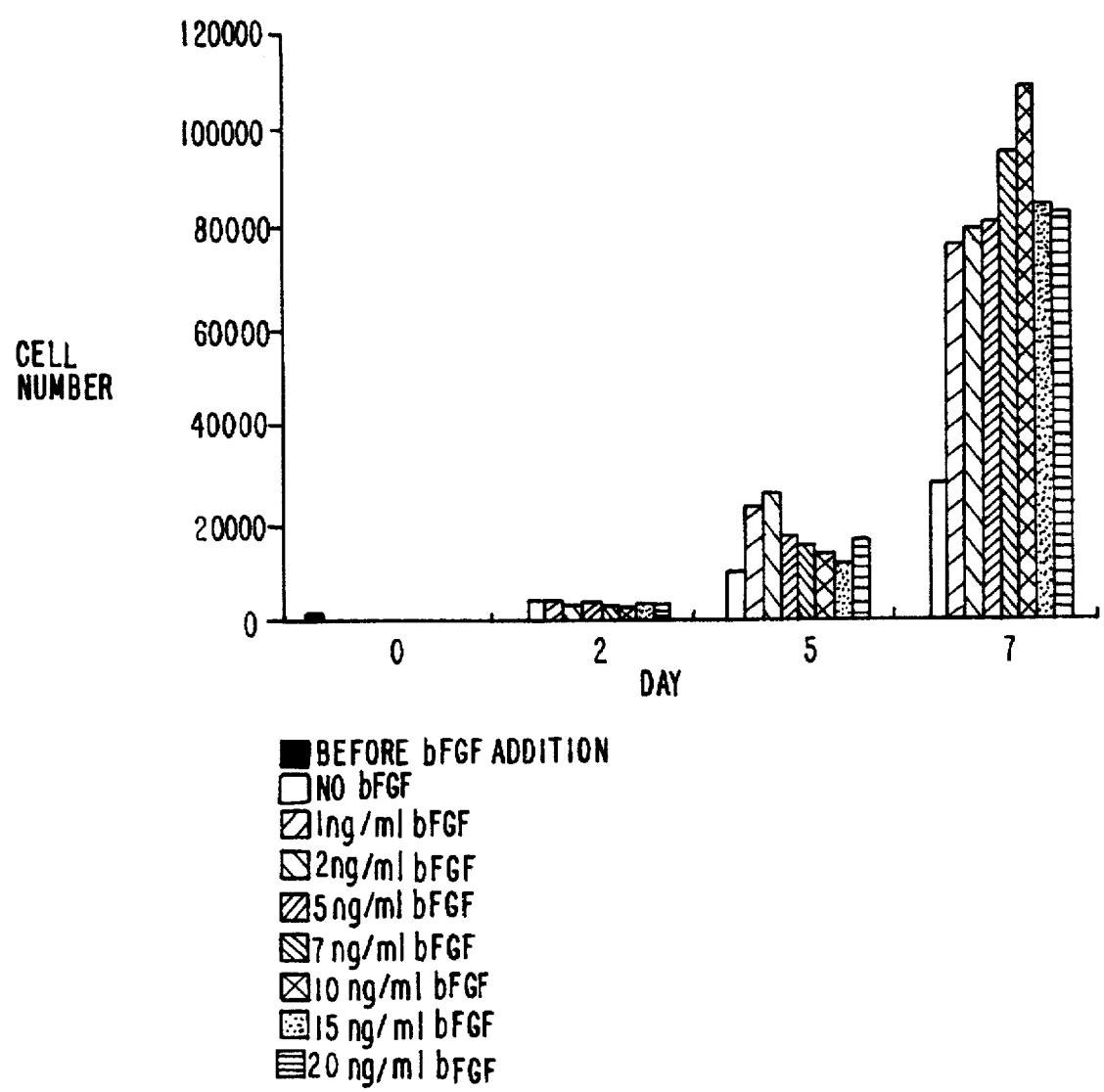
Figure 5:
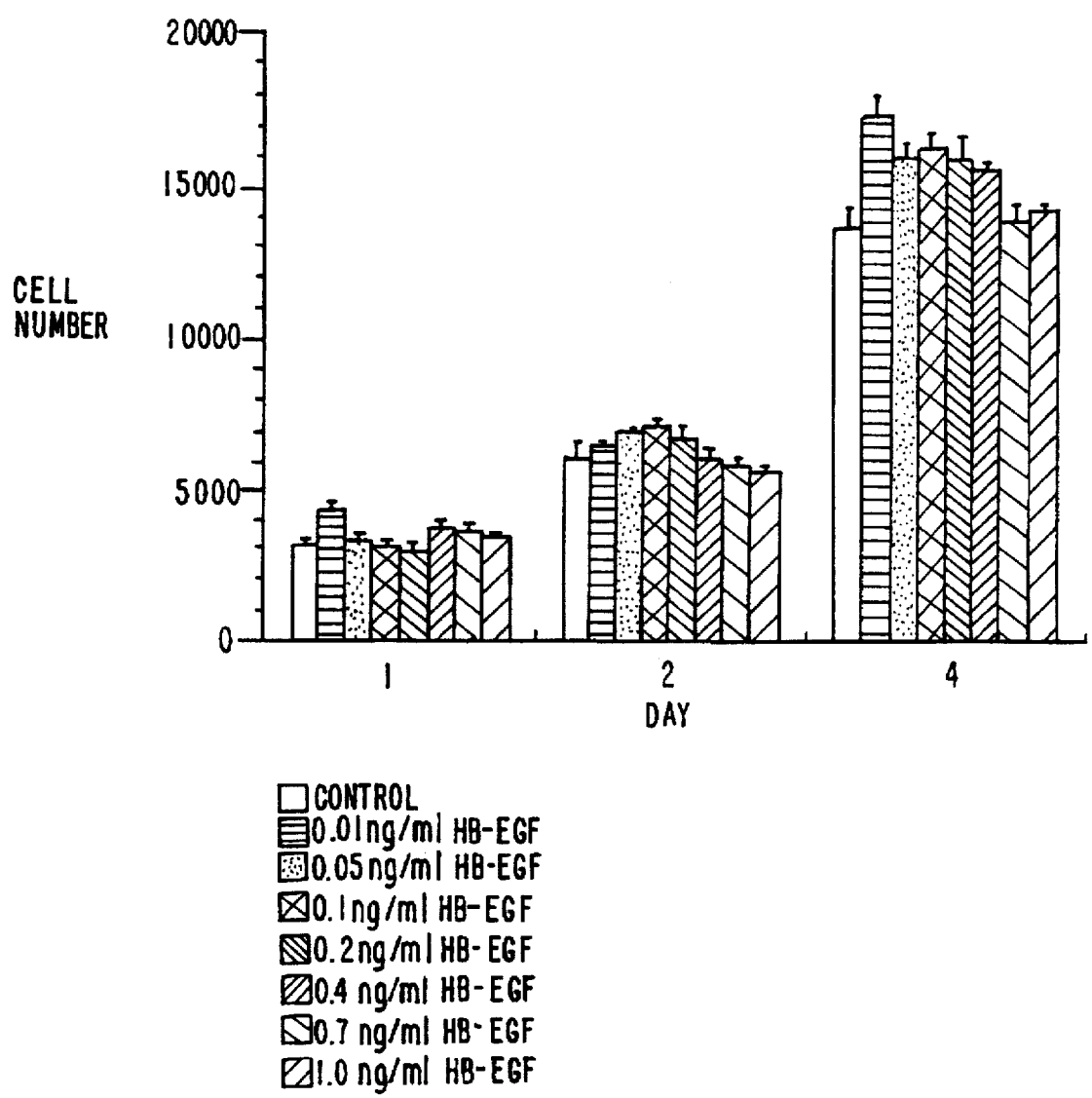
Figure 6:
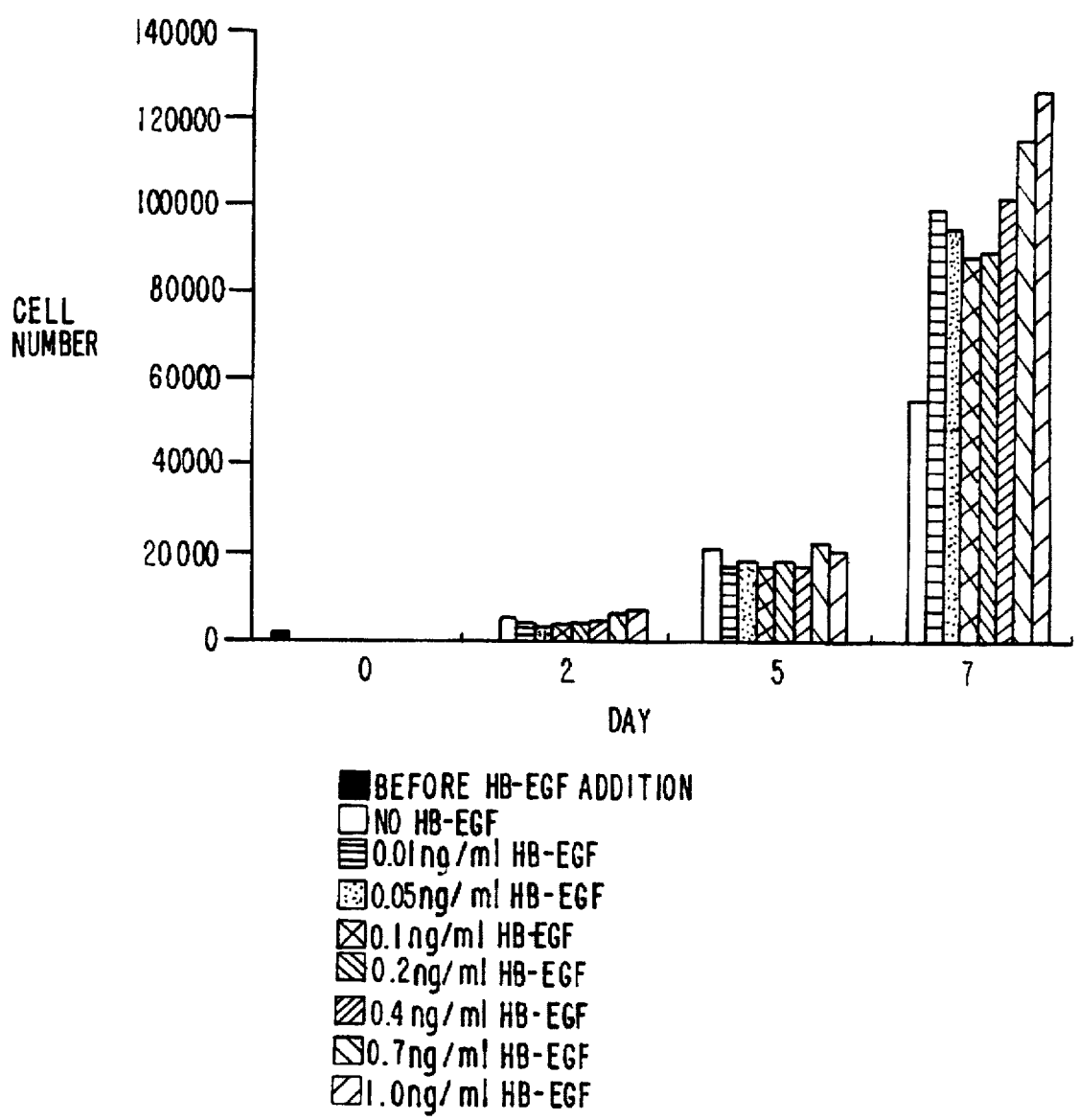
Figure 7:
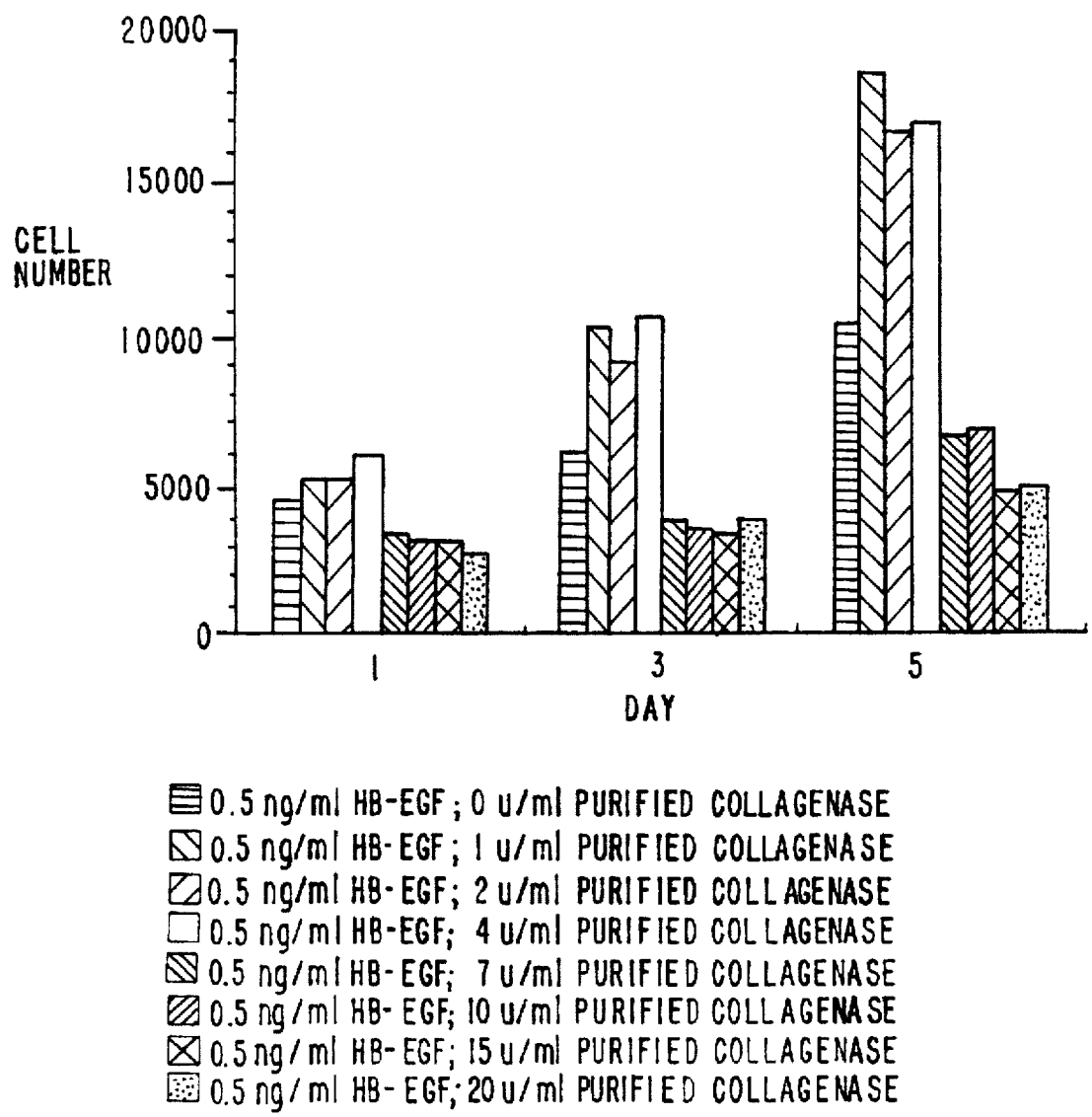
Figure 8:
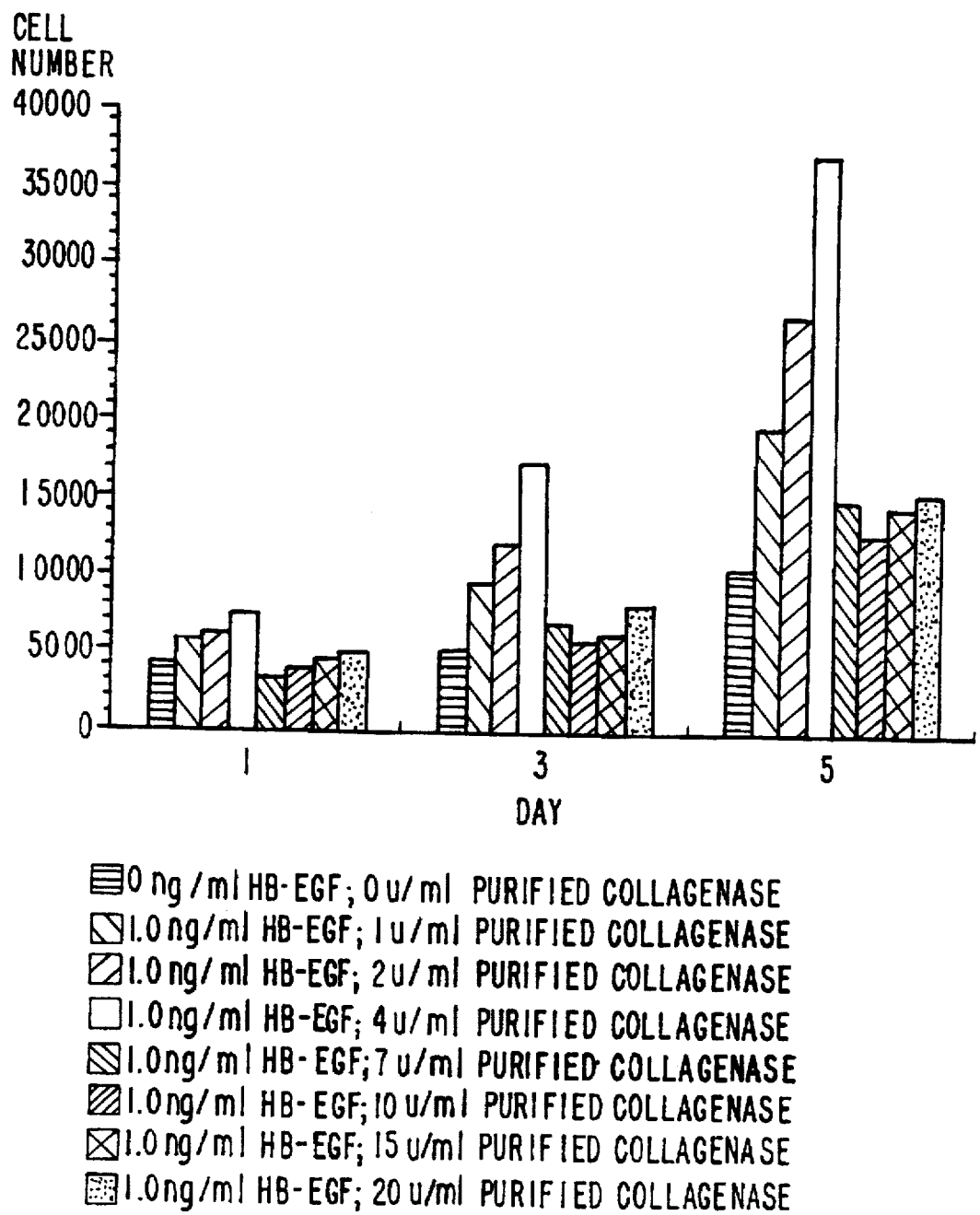

Table I gives the migration results in terms of Migration Index.

Table II gives the proliferation results in terms of Proliferation Index.

TABLE I

MATRIX MODULATES KERATINOCYTE SHEET MIGRATION

| Matrix | Migration Index (MI)$ |
|---|---|
| Untreated | 1.0 |
| ABC Purified Collagenase | 3.1 |
| Cleaned-Up Crude Collagenase | 2.4 |
| Crude collagenase | 1.9 |

$$\$MI = \frac{\text{mean motility (experiment)}}{\text{mean motility (control)}}$$

TABLE II

MATRIX MODULATION OF KERATINOCYTE PROLIFERATION

| Matrix | Proliferation Index (PI)$ |
|---|---|
| Untreated | 1.0 |
| ABC Purified Collagenase | 2.1 |
| Cleaned-Up Crude Collagenase | 1.4 |
| Crude Collagenase | 1.3 |
| Clostripain | 1.3 |
| Pool 3A | 1.3 |

$$\$PI = \frac{\text{mean cell counts (experiments)}}{\text{mean cell counts (control)}}$$

In these tests, treatment of the extracellular matrix with the purified collagenase potentiated keratinocyte migration 3-fold over the untreated matrix control, and potentiated keratinocyte proliferation 2-fold over the untreated matrix control. Other similar tests gave migration rates up to 10-fold over untreated matrix. Further in every instance the results with the purified collagenase were superior to those obtained with the less pure (cleaned up crude and crude) collagenases.

Another series of tests employed three kinds of synthetic sub-cellular matrices, prepared respectively from normal skin fibroblasts, endothelial cells, and cells from keloid scars. Each was treated with concentrations of purified collagenase ranging from 1 ABC unit/ml to 64 ABC units/ml, and the rate of cell growth (proliferation) is measured. With each matrix the growth rate at 64 units/ml was taken as the rate beyond which a higher dosage would have only limited effect. The dosage giving 50% of that growth rate (designated ED 50) was for each matrix about 1 ABC unit/ml.

SECTION B

The effects of various combinations of purified collagenase and growth factors on the motility and proliferation of keratinocytes were determined in vitro, employing subcellular matrices synthesized from vascular endothelial cells. The protocols did not vary a great deal from those described in SECTION A, unless noted otherwise. All collagenase used in this SECTION B was purified Clostridiopeptidase A substantially free from other proteinases. FIGS. III–X present graphically the experimental results.

FIG. 3

Basic fibroblast growth factor, human recombinant (bFGF) was added exogenously to the culture medium in which a plastic base was plated with human keratinocytes. No collagenase was used in this experiment. Media containing the various concentrations of BFGF were replaced every other day ("cell feeding"). Proliferation of the keratinocytes reached a maximum at 10 ng BFGF per ml.

FIG. 4

An experiment identical to that of FIG. III, but on a matrix, and with no collagenase used either on the matrix or exogenously. "Before BFGF addition" means this was the initial plating of cells before the media were changed to test media, either containing BFGF or not. As in FIG. III, the effect of BFGF reached a maximum at 10 ng/ml.

FIG. 5

The effect of heparin-binding epidermal-like growth factor (hb-EGF) on keratinocyte growth was determined in media containing increasing concentration of hb-EGF, with no matrix and no collagenase. At day 2, maximum was at 0.1 ng/ml. At day 4 it was at 0.01 ng/ml.

FIG. 6

Here the matrix was prepared from bovine retinal endothelial cells (BREC), according to the protocol in SECTION A above. No collagenase was used in this experiment. HB-EGF was added exogenously to the growth (culture) medium as described under FIG. IV above. At the seventh day, maximum growth of keratinocytes was achieved at the maximum concentration tested, 1.0 ng HB-EGF/ml.

FIG. 7

This experiment was performed on a purified collagenase-treated BREL matrix, maintaining from test to test a constant concentration of 0.5 ng/ml exogenous HB-EGF and an increasing concentration of exogenous collagenase. Maximum keratinocyte growth was at 1, 2 and 4 units/ml collagenase. At 7 units/ml and above, the growth was inhibited.

FIG. 8

This experiment was identical to that of FIG. VII, except that it used a constant concentration of 1.0 ng/ml of HB-EGF with consequent higher level of growth. Maximum growth was achieved at 4 units collagenase per ml, and 7 units/ml and above was inhibiting.

FIG. 9

Matrices derived from bovine retinal endothelial cells were treated with purified collagenase. In culture medium containing either 0 or 4 units/ml of purified collagenase, concentrations of HB-EGF ranging from 0.01 ng/ml up to 1.0 ng/ml were tested. The rate of human keratinocyte (HK) growth was potentiated at concentrations of 0.01, 0.05 and 0.1 ng/ml HB-EGF. Maximum growth was at 0.1 ng/ml, while 0.2 ng/ml and above were inhibiting. The data show that the addition of HB-EGF to keratinocytes growing on a purified collagenase-treated matrix in the presence of purified collagenase yields a growth promoting potential about 3.5-fold over untreated matrix controls.

FIG. 10

This figure shows the results of a survey of growth factors as they affect keratinocyte proliferation.

The first column shows the Proliferation Index in which the matrix has not been treated with collagenase nor was there any exogenous collagenase.

In the second column, the matrix was treated with purified collagenase.

The third column shows the result of using exogenous purified collagenase with the treated matrix.

The remaining columns show the proliferation indices when a wide range of related and unrelated growth factors were tested as exogenous solutions with treated matrix. The growth factors were Transforming growth factor, alpha (TGF alpha), Hepatocyte growth factor (HGF), Epidermal growth factor (EGF), acidic Fibroblast growth factor (FGF-1) (aFGF), basic Fibroblast growth factor (FGF-2) (bFGF), heparin-binding epidermal-like growth factor (hb-EGF). Additional ones to consider include platelet derived growth factor (PDGF), transforming growth factor-beta (TGF-beta), insulin-like growth factor (IGF), and keratinocyte growth factor (kGF).

It will be seen that none of the growth factors gave a Proliferation Index as great as that resulting from the use of collagenase. As shown in earlier Figures, combinations of growth factors plus collagenase are superior to either alone.

I claim:

1. A method of enhancing the migration and proliferation of keratinocytes in human wound healing which comprises contacting same with (a) an effective amount of purified Clostridiopeptidase A collagenase substantially free from other proteinases and (b) an amount of a growth factor that increases the effects of said collagenase.

2. A method according to claim 1 wherein said growth factor is a heparin-binding growth factor.

3. A method according to claim 2 wherein said growth factor is heparin-binding epidermal-like growth factor.

4. A method according to claim 1 wherein said collagenase is applied in the form of an aqueous solution containing from about 0.5 ABC units collagenase/ml to about 150 ABC units/ml.

5. A method according to claim 1 wherein said growth factor is applied in the form of an aqueous solution containing from about 0.01 ng/ml to about 10 ng/ml.

6. A method according to claim 1 wherein said growth factor binds to high-affinity receptors of keratinocytes.

7. A method according to claim 6 wherein said growth factors also binds at low affinity to the sub-cellular matrix.

8. A method of treating an open wound in human skin which comprises contacting the sub-cellular matrix underlying the wound with (a) purified Clostridiopeptidase A collagenase substantially free from other proteinases in a concentration effective to enhance the rate of migration of keratinocytes towards the wound edges and (b) a growth factor that binds to high-affinity receptors of keratinocytes in a concentration effective to increase the effectiveness of said collagenase in stimulating keratinocyte wound healing responses.

9. A method according to claim 8 wherein said growth factor is a heparin-binding growth factor.

10. A method according to claim 9 wherein said growth factor is heparin-binding epidermal-like growth factor.

11. A method according to claim 8 wherein said collagenase is applied in the form of an aqueous solution containing from about 0.5 ABC units collagenase/ml to about 150 ABC units/ml.

12. A method according to claim 8 wherein said growth factor is applied in the form of an aqueous solution containing from about 0.1 ng/ml to about 1.0 ng/ml (i.e. hb EGF).

13. A method of enhancing the migration and proliferation of keratinocytes in mammalian wound healing which comprises contacting same with (a) an effective amount of purified Clostridiopeptidase A collagenase substantially free from other proteinases and (b) an amount of a growth factor that increases the effects of said collagenase.

14. A method according to claim 13 wherein said growth factor binds to high-affinity receptors of keratinocytes.

15. A method according to claim 14 wherein said growth factor also binds at low affinity to the sub-cellular matrix.

16. A method of treating an open wound in mammalian skin which comprises contacting the sub-cellular matrix underlying the wound with (a) purified Clostridiopeptidase A collagenase substantially free from other proteinases in a concentration effective to enhance the rate of migration of keratinocytes towards the wound edges and (b) a growth factor that binds to high affinity receptors of keratinocytes in a concentration effective to increase the effectiveness of said collagenase in stimulating keratinocyte wound healing responses.

* * * * *